Figure 1:
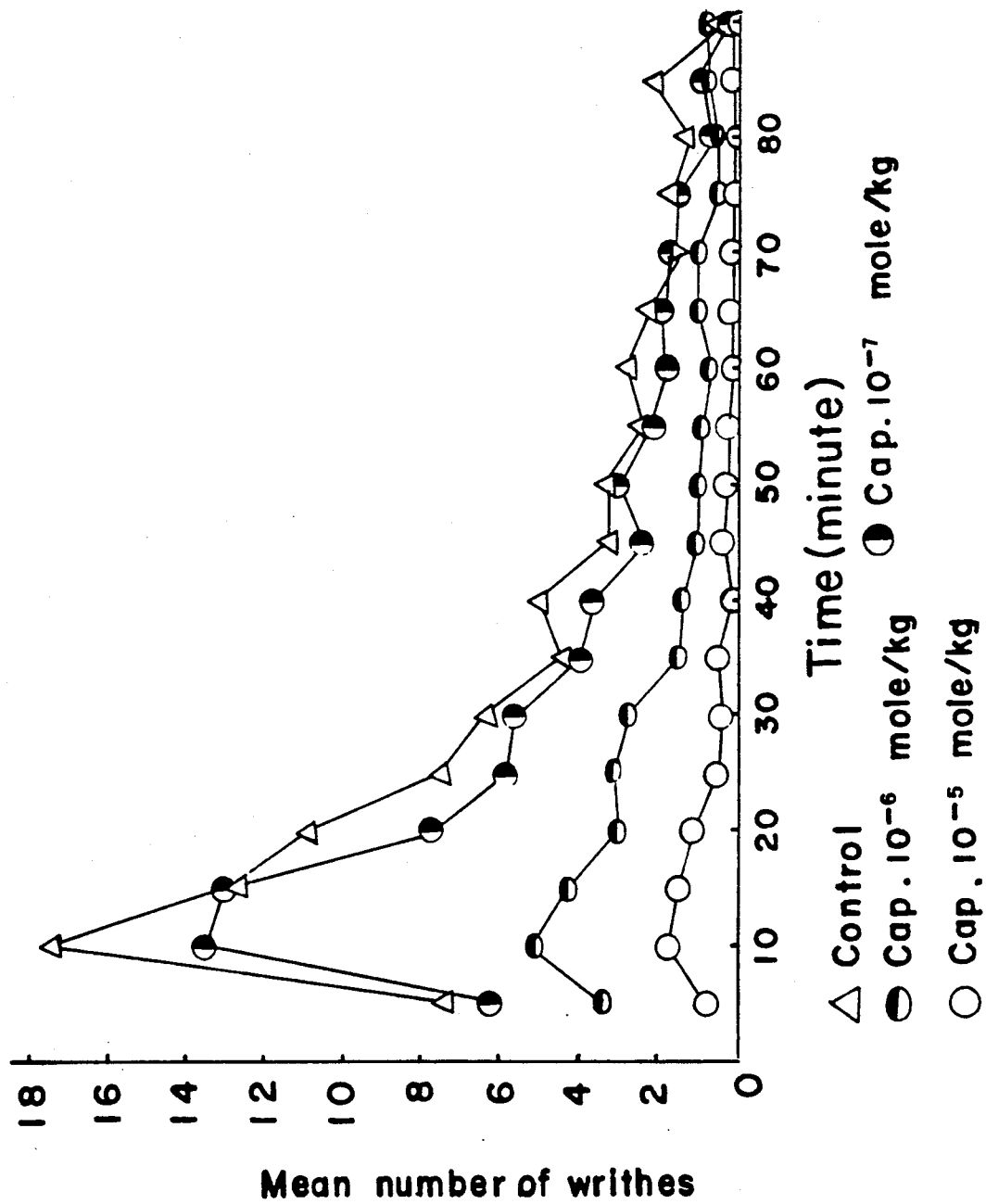

United States Patent [19]

Chen et al.

[11] Patent Number: 5,094,782

[45] Date of Patent: Mar. 10, 1992

[54] SYNTHESIS OF CAPSACIN DERIVATIVES AND THEIR USE AS AN ANALGESIC DRUG AND VESSEL DILATION DRUG

[75] Inventors: Chen; Jwu-Lai Yeh, both of Taipei, Taiwan

[73] Assignee: National Science Council of Republic of China, Taipei, Taiwan

[21] Appl. No.: 632,525

[22] Filed: Dec. 24, 1990

[51] Int. Cl.$^5$ ............................................. C09F 7/00
[52] U.S. Cl. ........................................................ 260/404
[58] Field of Search ........................................ 260/404

[56] References Cited

PUBLICATIONS

Nelson, Journal of the American Chemical Society, vol. 45, pp. 2170-2181, 1923.

*Primary Examiner*—José G. Dees
*Assistant Examiner*—Deborah D. Carr
*Attorney, Agent, or Firm*—Fleit, Jacobson, Cohn, Price, Holman & Stern

[57] ABSTRACT

Nonanoyl vanillylamide succinate was synthesized from synthetic capsaicin (nonanoyl vanillylamide) and succinic anhydride. The antinociceptive and cardiovascular effects of nonanoyl vanillylamide and its derivatives were investigated. We found that nonanoyl vanillylamide and nonanoyl vanillylamide succinate strongly inhibited the writhing response, led to the vascular smooth muscle relaxation, produces bradycardia and a fall of blood pressure. The potency of nonanoyl vanillylamide succinate was found to be slight greater than that of nonanoyl vanillylamide, when compared with the same molar dose/kg of their administrations.

4 Claims, 3 Drawing Sheets

SYNTHESIS OF CAPSACIN DERIVATIVES AND THEIR USE AS AN ANALGESIC DRUG AND VESSEL DILATION DRUG

BACKGROUND OF THE INVENTION

The hot peppers from the species *Capsicum annuum L., C. frutesscens L.* and *C. minimum L.* have been consumed as food by mankind for some periods of time. The active ingredient, 8-methyl-N-vanillyl-6-nonenamide (capsaicin), was isolated and identified by Nelson. (Nelson, E. K., *J. Am. Chem. Soc.* 45, 2179-2181, (1923).) and here after studies concerning its physiological and pharmacological effects on animals had been carried out. Skofitsch (Skofitsch, G. Donnerer, J. Petronijevic, S., Saria, A., and Lembeck, F., *Naunyn-Schmiedebergs Arch. Pharmacol.* 322, 153-157, 1983.) showed that capsaicin can selectively activate the vagal C-fiber afferents in the airways and can also stimulate the central nervous system (CNS) and the local reflex systems to release some biologically active peptides. Lundberg (Lundberg, J. M., Brodin E., and Saria, A., *Acta. Physiol. Acand.,* 119, 243-252, (1983).) found out that when the compound was sprayed on the respiratory organ of the animal, it can cause the release of substance P and CGRP (calcitonin gene related peptide) of the airways. When the mucus of the experimental felines were treated with capsaicin, local mucosal bleeding was observed via the stimulation of the C-fiber afferents. These agents were also observed to increase the permeability of blood vessels so as to cause the extravasation of proteins. Later researches in this area (Toh, C. C., Lee, T. S., and Kiang, A. K., *Brit. J. Pharmacol.,* 10, 175-182, (1955), Coleridge, H. M., Coleridge, J. C., and Kidd, C., *J. Physiol., London,* 170, 272-285, (1964), Virus, R. M., and Gebhart, G. F., *Life Sci.,* 25, 1273-1284, (1979).) indicate that capsaicin has overt effects in the dilation of the aorta, lowering the blood pressure and slowing down the heart rate.

Recent studies in the biochemistry of capsaicin show that it can enhance the activity of hormone sensitive lipase (HSL) in fatty tissues but can inhibit the activities of $Ca^{2+}$, calmodulin dependent cyclic AMP and phosphodiesterase (PDE) in adipose tissues. As a result of these lipolytic activity, it can also be used to lower the lipid level in blood. Further more capsaicin was also found to inhibit the aggregation of blood platelets. Even though many pharmacological researches confirm the effects of capsaicin on the cardiovasular system, its properties as a potent stimulant (spicy sensation even at a 1/8000 mg concentration) and as a neurotoxic agent (extravasation of peptides, airways smooth muscle contraction) coupled with the fact that it is only sparingly soluble in water have greatly retarded the efforts towards developing the compound as a clinically useful agent. As long as concerning of improving its aqueous solubility, solvents such as: alcohols, DMSO and Tween 80 had been employed; but all these had shown to affect its natural pharmacological profile. The intent of the present invention is to introduce a hydrophilic moeity to the structure so as to improve its water soluble property. The followings are the detail disclosure of the invention.

DISCLOSURE OF INVENTION

Presently, the research efforts on the pharmacological effect of capsaicin mainly involve using alcohol, dimethylsulfoxide or Tween 80 or other organic solvents as the vehicle to dissolve capsaicin. This invention intends to modify the aqueous solubility of capsaicin by introducing a hydrophilic moiety.

I. SYNTHESIS OF CAPSAICIN DERIVATIVE OR NONANOYL VANILLYLAMIDE SUCCINATE

The synthetic capsaicin derivatives were prepared by reacting nonanoyl vanillylamide with succinic anhydride to yield nonanoyl vanillylamide succinate.

The active ingredient isolated by Nelson et. al. is 8-methyl-N-vanilly-6-nonenamide (capsaicin) and has the following chemical structure.

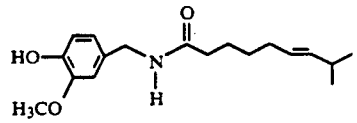

The compound has an empirical formula of $C_{18}H_{27}NO_3$ and a melting point of 65° C. It is practically insoluble in cold water but solubility increases as temperature rises. It is readily soluble in alchols, benzene, ether and chloroform. Its UV shows £ f $_{max}$ at 227 and 281 nm. The double bond unit on the side chain may potentially cause complex unpredictable chemical reactions such as electrophilic or nucleophilic addition or double bond formation or cleavage. Nelson et. al had done some detail studies on the effect of the side chain on the overall biological activity. What they observed was that whether the side chain was shortened or prolongated via the cleavage or addition to the double bond unit, the spicy sensation decreased. However, the activity was enhanced by the solubility of the compound in aqueous solution. Jones and coworkers (Jones, E. C. S. and Pyman, F. L., *J. Chem. Soc.*, 127, 2588, (1925).) examined the methylation of the phenolic unit and found out that this also decreases the spicy sensation. Based on the aforementioned information, we tried to take all possible factors (the difficulty of the operation, the efficiency in the yield and the complexity of the intermediates etc.) into consideration and decided that the best approach was to saturate the side chain in the first stage and a hydrophilic unit would then be put on afterwards to enhance its solubility in water. Later on the development, we discovered that a TCI product, nonanoyl vanillylamide (also as N-perlargonyl vanillylamide), was a perfect starting material for our study.

The compound has the following structure and characters:

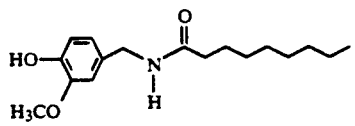

The compound has an empirical formula of $C_{17}H_{27}NO_3$ and a melting point of 42°–45° C. Its UV shows $\lambda_{max}$ at 227 and 276.5 nm. It is a synthetic material and is slightly soluble in cold water but very soluble in hot water, alchol, ether and chloroform. The pharmacological properties between nonanoyl vanillyamide and capsaicin had been examined by Northan et. al. (Northan, W. j. and Jones, D. J., *Life Sci.,* 35, 293-302, 1561-1568. (1984); Szolcsanyi, J., and Janco-Gabor, A. *Drug Res.* 25, 1877, (1975); Bucsics, A. and Lembeck, F., *Eur. J. Pharmacol.*, 71, 71-77. (1981); Fujh, T., Ohbuchi, Y., Takahashi, S., Sakurada, T., Sakurada, S., Ando, R. and Kisara, K. *Arch. Int. Pharmacodyn.* 280, 65-176. (1986).) and it was found that their activities are rather similar. It was therefore envisioned that the operation could be simplified by employing the nonanoyl vanillylamide directly as the starting material for the introduction of the hydrophilic unit and the prior saturation step could therefore be deleted from the scheme.

The present invention describes the implementation of the above strategy and via the employment of a catalyst at 10°-100° C., the hydrophilic moiety was introduced onto nonanoyl vanillylamide. The volatile components were removed in vacua and the residue was purified on a silica gel column to recover the product. Nevertheless, for the aforementioned procedure, the yield was low and also it was time consuming and therefore the operation was modified to improve the efficiency of the process.

II. SEPARATION OF NONANOYL VANILLYLAMIDE/NONANOYL VANILLYLAMIDE SUCCINATE

The target compound was isolated by extraction and recrystallization (scheme I) rather than by silica gel column because of its ineffectiveness.

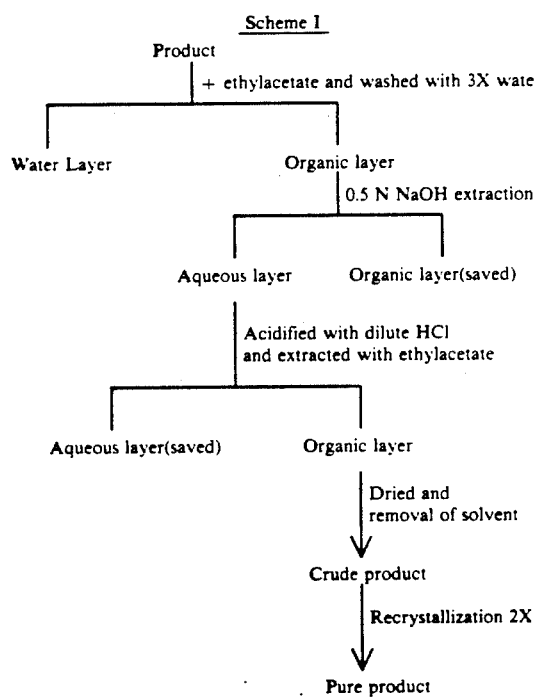

The product was first extracted into ethyl acetate and after washing with water, the organic layer was extracted with dilute NaOH to transfer the desired compound to the aqueous layer, which was then acidified with dilute HCl and back extracted into an ethyl acetate layer. The organic layer was dried and after removal of the solvent, the crude product was recrystallized to give the pure compound. The product, as expected, was soluble in mildly basic aqueous layer (e.g. 0.1% sodium carbonate). Therefore, this property was later explored to acquire a water soluble formulation. And its stability can be estimated by its UV absorption and all the other physical and spectral properties, such as melting point, IR, NMR and MS, were also examined and found to be different from the standard.

III. THE PHYSICAL PROPERTIES OF NONANOYL VANILLYLAMIDE SUCCINATE:

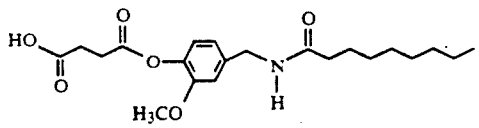

The pure nonanoyl vanillylamide succinate appears as white needle crystals (from benzene) with a melting point of 104°-106° C. TLC(benzene: ethyl acetate 1:1, v/v) shows a Rf of 0.3 and the spot is light pink in color when treated with methanbolic 2,6-dichlorphenolindophenol sodium. Elemental analysis indicates an empirical formula of $C_{21}H_{31}NO_6$ (calcd. C 64.10%, H 7.94%, N 3.56%, found C 63.79%, H 7.90%, N 3.57%) which is different from the starting material supplied by TCI (C 69.69%, H 9.45% N 4.79%). The IR spectrum (KBr) indicates carbonyl absorptions at 1698 $cm^{-1}$ and broad peak for the carboxylic acid at about 1700 $cm^{-1}$. Compared with the IR of capsaicin, it is observed that the 3450 $cm^{-1}$ for OH has disappeared. The M.S. shows a $M^+$ peak at 393. NMR($CDCl_3$, TMS): ppm 0.87 (3H, Me), 1.25-2.25 (14H, $CH_2$), 2.77-2.90 (4H, $CH_2$), 3.75 (3H, OMe), 4.34 (2H, $C_6H_5CH_2$), 6.32 (1H, NH), 6.76-6.97 (3H, aromatic), 9.92 (1H, COOH); $^{13}C$ NMR ($CDCl_3$): ppm 14.1, 22.7, 25.9, 28.9, 29.1, 29.2, 29.4, 31.9, 36.7, 43.5, 56.0, 112.4, 120.3, 123.1, 137.7, 139.3, 151.5, 171.2, 174.5, 177.1, 177.3. A total of 4 more peaks was observed when compared with the $^{13}C$ of nonanoyl vanillylamide. UV £ $f_{max}$: 210, 275 and 279 nm. All indications allude that the compound is indeed a new derivative of capsaicin.

IV. THE PHARMACOLOGICAL PROPERTIES OF NONANOYL VANILLYLAMIDE AND NONANOYL VANILLYLAMIDE SUCCINATE

The present invention is concerned with the modified derivatives of capsacin. Since the derivative(s) is/are soluble in mild alkaline solution, it is out intention then to make it a clinically useful antinociceptive and vascular dilating agent.

I.P. injection of nonanoyl vanillylamide or nonanoyl vanillylamide succinate can retard the abdominal contraction frequency in experimental mice. The inhibition on damages caused by 0.2 ml of a 0.7% acetic acid solution was found to be dose dependent ($10^{-7}$, $10^{-6}$ and $10^{-6}$ and $10^{-5}$ mol/kg). In vitro study of the effects of nonanoyl vanillylamide or its succinate on the isolated aorta of guinea pigs indicates that it can decrease the smooth muscle tension caused by phenylephrine; nevertheless, repetitive administrations will cause rapid and prolonged contractions which do not disappear even on furter treatment with nonanoyl vanillylamide or its succinate.

I.V. injection of nonanoyl vanillylamide or its succinate can cause the slowing down of heart rate, hypotension and the inhibition of respiration in Wistar rats. The i.v. administration of either reagent has three effects on the blood pressure:
a) The initial drop in blood pressure.
b) The rebounce of blood pressure.
c) A prolonged decrease in blood pressure.

These effects are nto affected by the presence of atropine, propanolol or phentolamine, but the initial pressure dropping effect(effect (a) can be inhibited by the removal of the vagus nerves on both sides. When the aorta was pretreated with nonanoyl vanillylamide succinate, the onset time was found shorter, but this cannot decrease the length of the arrhythmic reaction. In conclusion, nonanoyl vanillylamide succinate can effectively inhibit the writhing reaction, dilate the vascular smooth muscle, decrease the blood pressure, and slow down the heart beat. When comparing the strength of nonanoyl vanillylamide and its succinate, it was found that the succinate is somewhat more potent.

Its pharmacological properties on pain suppression and the cardiovascular system were also studied. Acetylcholine, acetic acid or phenylquinone were used as stimulants by i.p. injection on experimental mouse and the antinociceptive effect was examined by the extent of the writhing syndrome. The investigation was carried out along side with nonanoyl vanillylamide as the control standard. It was found that for the compounds examined, the pain suppression effect is proportional to the dosage applied and the potencies of both are rather similar. Its activities on the circulation system includes the vascular dilation effect and lowering of the blood pressure. Its effect with phenylephrine hydrochloride was also studied. Phenylephrine is known to cause the construction of the aorta in guinea pigs and therefore the inhibition of this phenomenon should indicate the effect of the agent. Both the nonanoyl vanillylamide and the synthetic nonanoyl vanillylamide succinate demonstrate the vascular dilation effect and the extent is proportional to the dosage applied; nevertheless, to our delight, the succinate overtly has a better potency than the nonanoyl vanillylamide.

According to Donnerer and coworkers (Donnerer, J. and Lembeck, F., *Naunyn-Schmiedebergs Arch. Pharmacol.* 324, 293-295, (1983).), when 250 nmole of capsaicin was introduced via i.v. into the Wistar rats under sedation, a triad response (Benzold Jarish response), namely the bradycardia, hypotension and apnea was observed. In our present investigations, similar effects were observed for both the nonanoyl vanillylamide and the succinate at a level of 25 and 250 nmole/kg. The triphasic blood pressure response, the rapid initial dropping of the blood pressure, the gradual rise to slightly above normal and then the prolonged hypotensive effect afterwards, was also noticed for both agents. The above observations were found to be quite reproducible. Also observed was that both the nonanoyl vanillylamide and the succinate do not seem to have obvious tachyphylaxis properties on blood pressure and heart rate.

EXAMPLE 1

To 3 mmole of nonanoyl vanillylamide in 30 mL of DMF, 3 mmole of succinic anhydride was added and the resulting mixture was stirred at 110° C. for 2-3 h. The reaction was monitored by TLC and at the end of the period, the reaction was cooled to room temperature and the DMF was removed in vacua. After appropiate amount of ethyl acetate was added, the reaction mixture was poured into a separatory funnel and the organic layer was first washed three times with water followed by the extraction with 0.5N NaOH. The alkaline solution was acidified with dilute hydrochloric acid and back extracted into ethyl acetate. The organic layer was dried (MgSO₄) and concentrated under reduced pressure. To the residue, hot benzene was added and filtered and after sitting at room temperature for about one day, the succinate was settled out as a white crystalline material. The product thus obtained was recrystallized again with benzene/n-hexane to yield the pure nonanoyl vanillylamide succinate (42%). The succinate thus obtained was further purified by recrystallization with benzene to yield a white needle crystal with a melting point of 104°-106° C. and a Rf of 0.3 on a silica gel TLC (benzene/ethyl acetate 1:1).

EXAMPLE 2

The Antinociceptive Effect

Figure 2:
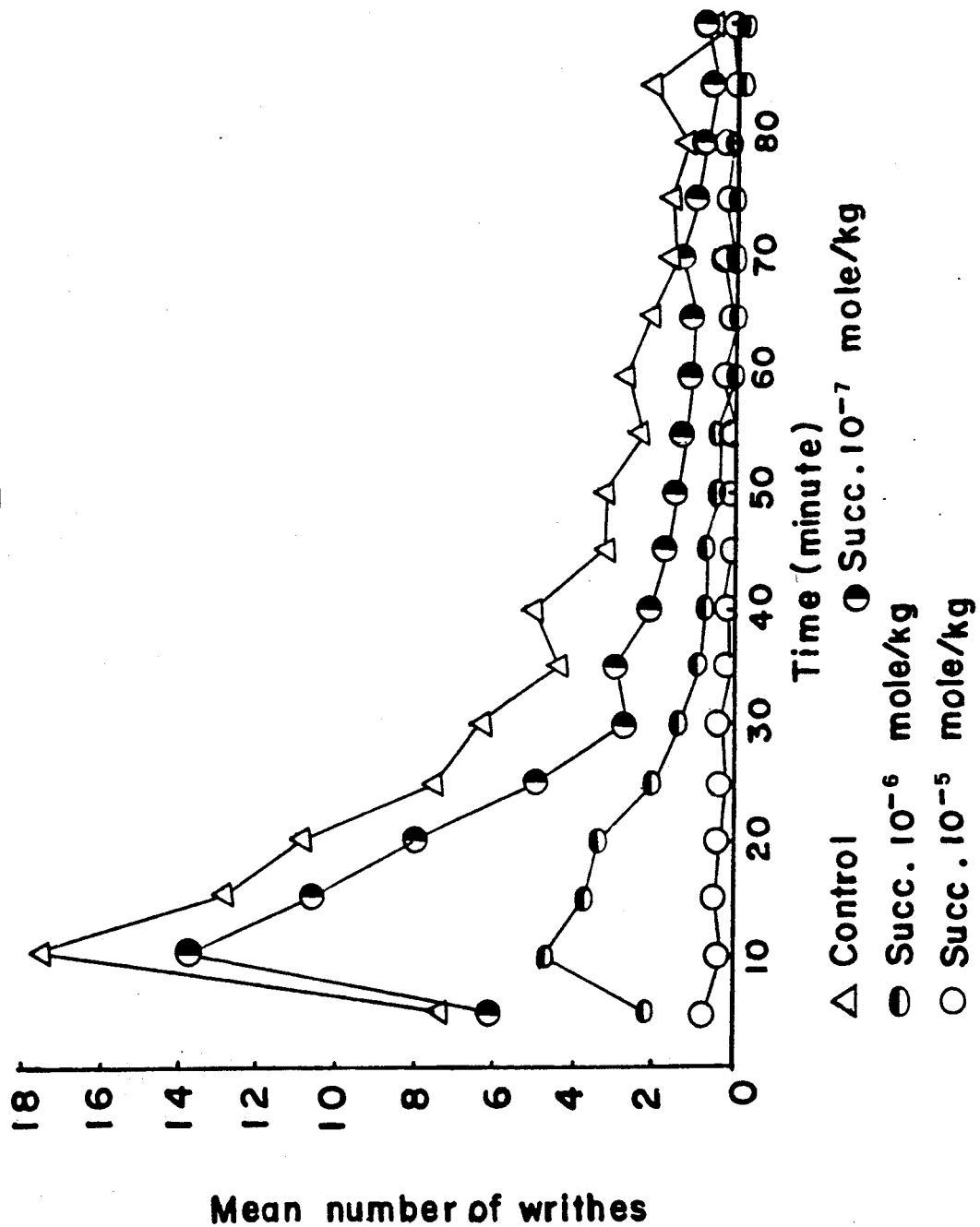

A modification of Koster's method was used. Thus a 0.7% acetic acid solution was administered by i.p. to the control set of mice and after 30 minutes the frequency in abdominal contraction (writhing syndome) was measured. For the other sets of animals, a dosage of $10^{-7}$, $10^{-6}$ and $10^{-5}$ nmole/kg of the nonanoyl vanillylamide or the nonanoyl vanillylamide succinate was introduced (i.p.) 30 minutes before the administration of the acetic acid stimulant and the results were shown at FIG. 1 and FIG. 2.

EXAMPLE 3

Cardiovascular Effects

Figure 3:
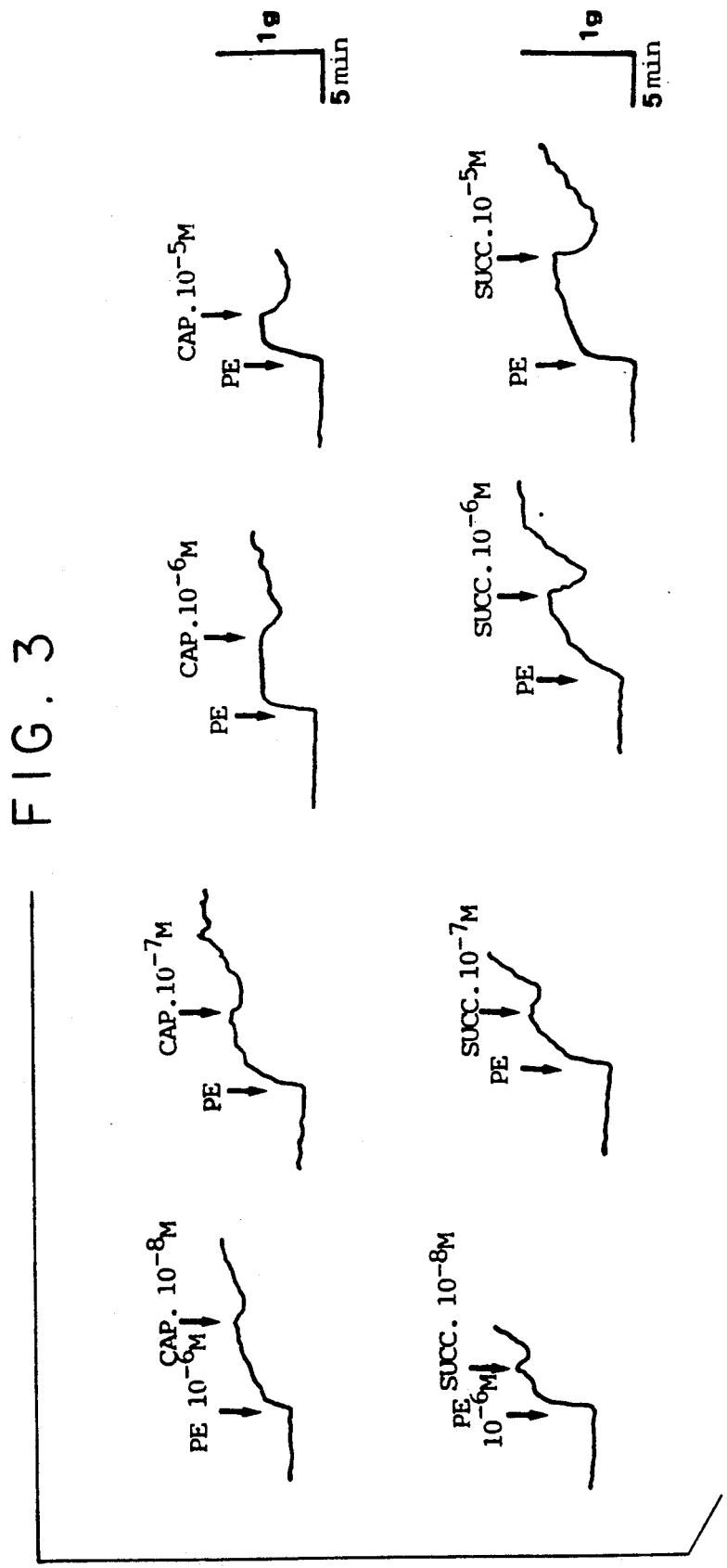

An isolated guinea pig aorta was immersed in a modified Krebs solution at a phenylephrine hydrochloride concentration of $10^{-6}$M. The vascular smooth muscle contraction for this control set was then measured and calculated as below. To the other sets of animals, nonanoyl vanillylamide and its derivatives at the concentrations of $10^{-8}$, $10^{-7}$, $10^{-6}$ and $10^{-5}$M were also introduced to the Krebs/phenylephrine solution. The result was shown in FIG. 3.

$$\% = \frac{\text{relaxation}}{\text{contraction}} \times 100\%$$

What is claimed is:

1. A compound of nonanoyl vanillylamide succinate having the structural formula of:

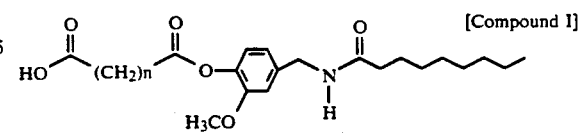

[Compound I]

wherein, n is from 2 to 4.

2. A process for the preparation of a compound of nonanoyl vanillylamide succinate having a structural formula as set forth in claim 1 comprising:
   (a) reacting nonanoyl vanillylamide with an anhydride in a polar solvent to form a succinate of said nonanoyl vanillylamide; and
   (b) purifying said succinate by separating said succinate from said polar solvent.

3. The process as claimed in claim 2 wherein the polar solvent is selected from the group consisting of: dimethylformamide, tetrahydrofuran, dimethylsulfoxide, dimethylacetamide, dioxane, nitromethane, acetone, and acetonitrile.

4. The process as claimed in claim 2 wherein the anhydride is selected from the group consisting of: succinic anhydride, glutaric anhydride, adipic anhydride and their substituted analogs.

* * * * *

UNITED STATES PATENT AND TRADEMARK OFFICE
CERTIFICATE OF CORRECTION

PATENT NO. : 5,094,782

DATED : March 10, 1992

INVENTOR(S) : Ing-Jun CHEN et al

It is certified that error appears in the above-identified patent and that said Letters Patent is hereby corrected as shown below:

On the Title Page, Item [75], the correct spelling of the first inventor's name is --Ing-Jun Chen--.

Signed and Sealed this

Seventeenth Day of August, 1993

Attest:

BRUCE LEHMAN

Attesting Officer

Commissioner of Patents and Trademarks